(12) United States Patent
Hanasaka

(10) Patent No.: US 12,149,824 B2
(45) Date of Patent: Nov. 19, 2024

(54) EXAMINATION APPARATUS, CONTROL METHOD THEREOF, AND OPHTHALMIC APPARATUS

(71) Applicant: CANON KABUSHIKI KAISHA, Tokyo (JP)

(72) Inventor: Takashi Hanasaka, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 521 days.

(21) Appl. No.: 17/587,040

(22) Filed: Jan. 28, 2022

(65) Prior Publication Data

US 2022/0247935 A1   Aug. 4, 2022

(30) Foreign Application Priority Data

Feb. 1, 2021   (JP) .................. 2021-014432

(51) Int. Cl.
*H04N 23/67*   (2023.01)
*A61B 3/14*    (2006.01)
*G06T 7/00*    (2017.01)
*H04N 23/56*   (2023.01)
*A61B 3/12*    (2006.01)

(52) U.S. Cl.
CPC ............. *H04N 23/672* (2023.01); *A61B 3/14* (2013.01); *G06T 7/0012* (2013.01); *H04N 23/56* (2023.01); *A61B 3/12* (2013.01); *G06T 2207/30041* (2013.01)

(58) Field of Classification Search
CPC .... H04N 23/672; H04N 23/56; H04N 25/134; H04N 25/704; A61B 3/14; A61B 3/12; A61B 3/13; G06T 7/0012; G06T 2207/30041

USPC .......................................................... 351/206
See application file for complete search history.

(56) References Cited

U.S. PATENT DOCUMENTS

| 4,410,804 A * | 10/1983 | Stauffer ................. G06V 20/64 |
| | | 348/42 |
| 9,004,684 B2 | 4/2015 | Iwanaga et al. |
| 9,488,898 B2 * | 11/2016 | Inoue ................... H04N 25/134 |
| 9,509,897 B2 * | 11/2016 | Aoki .................... H04N 23/672 |

(Continued)

FOREIGN PATENT DOCUMENTS

JP   2009-261573 A   11/2009

*Primary Examiner* — William R Alexander
(74) *Attorney, Agent, or Firm* — Cowan, Liebowitz & Latman, P.C.

(57) ABSTRACT

An ophthalmic apparatus is provided with an image capturing optical system and an image capturing apparatus, and optically examines an eye to be examined by performing focus detection using image capturing surface phase difference AF. A focus detection unit calculates data for a focus detection precision map from a defocus amount based on the phase difference detection. In a case in which the focus detection precision of a first subject is less than an established precision, a region determining unit determines a circle or concentric circle region that passes through the first subject, and determines a region that includes a second subject on the focus detection precision map included on the circle or inside of the concentric circle region, and that also has a focus detection precision that is higher than a predetermined precision. The focus detection unit then performs focus detection on the second subject.

9 Claims, 14 Drawing Sheets

(56) References Cited

U.S. PATENT DOCUMENTS

| | | | | |
|---|---|---|---|---|
| 2005/0068614 A1* | 3/2005 | Yoneyama | ............ | G02B 21/245 |
| | | | | 359/383 |
| 2008/0123185 A1* | 5/2008 | Yoneyama | .............. | G02B 21/16 |
| | | | | 359/383 |
| 2008/0204865 A1* | 8/2008 | Yoneyama | .............. | G02B 21/16 |
| | | | | 359/392 |
| 2014/0016021 A1* | 1/2014 | Uchida | ................ | H04N 25/704 |
| | | | | 348/353 |
| 2014/0267839 A1* | 9/2014 | Nishimaki | .............. | H04N 25/68 |
| | | | | 348/246 |
| 2014/0340567 A1* | 11/2014 | Fukuda | ................ | H04N 23/672 |
| | | | | 348/353 |
| 2015/0229834 A1* | 8/2015 | Aoki | ....................... | G02B 5/201 |
| | | | | 348/345 |
| 2015/0286112 A1* | 10/2015 | Inoue | .................. | H04N 25/134 |
| | | | | 348/357 |
| 2018/0255231 A1* | 9/2018 | Fukuda | .................. | H04N 23/67 |

\* cited by examiner

FIG. 3A
FIG. 3B
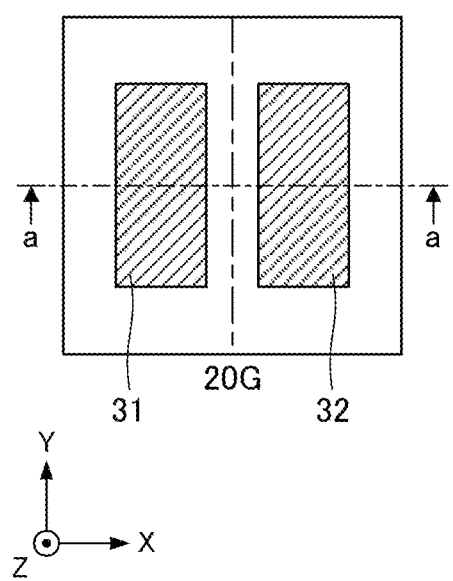
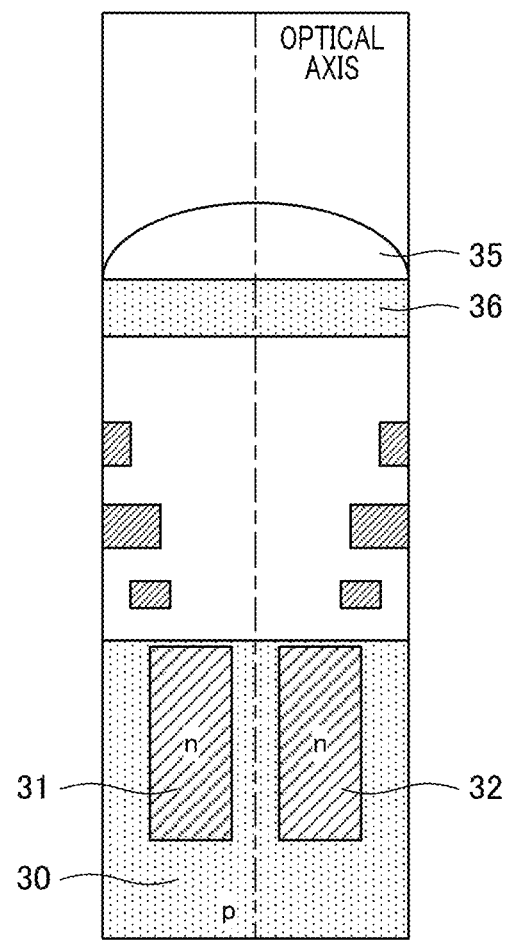

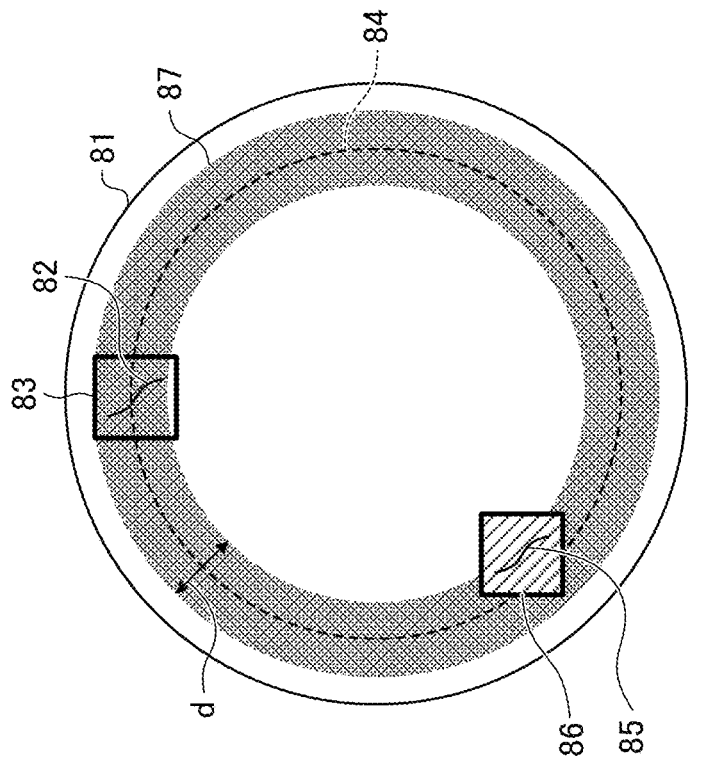
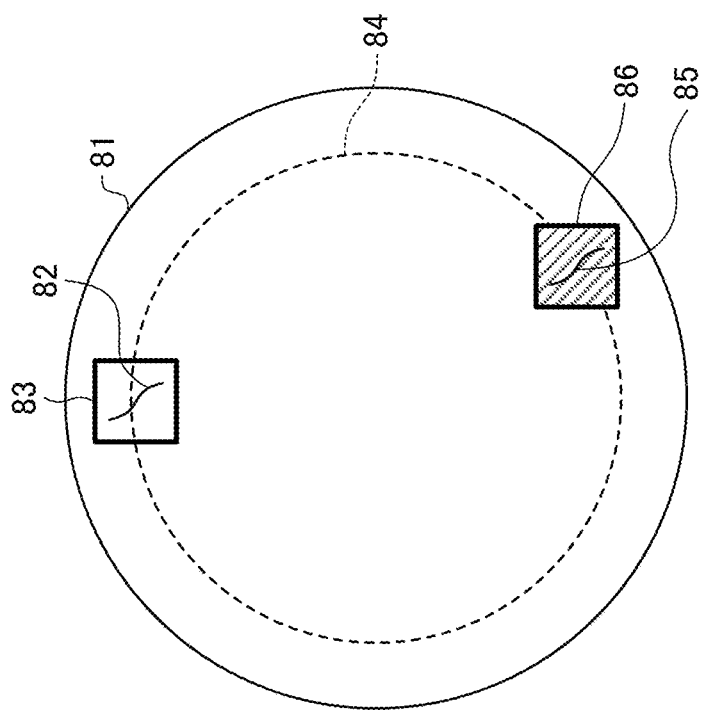

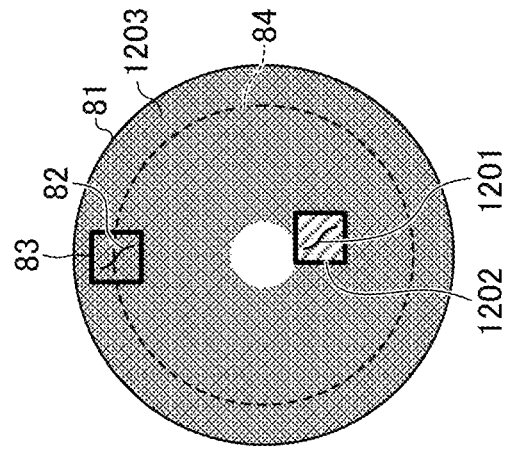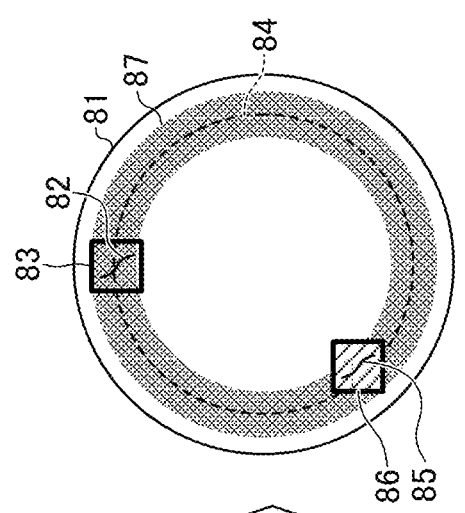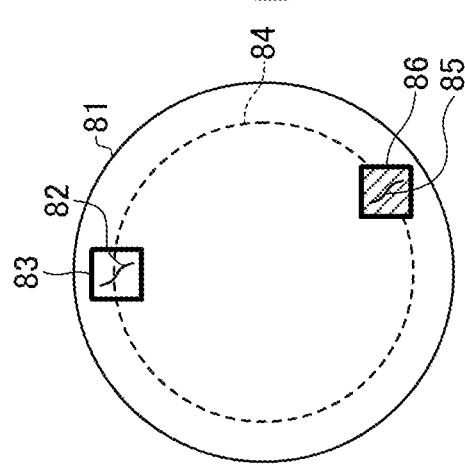

EXAMINATION APPARATUS, CONTROL METHOD THEREOF, AND OPHTHALMIC APPARATUS

BACKGROUND OF THE INVENTION

Field of the Invention

The present invention relates to an examination apparatus that optically examines an examination subject.

Description of Related Art

Ophthalmic apparatuses that capture images of the fundus of the eye of an examination subject are used in ophthalmology clinics and the like. In ophthalmic apparatuses, in order to focus on an eye to be examined, there is a method of performing autofocusing (referred to below as AF) based on the positional relationship of a split image that has been segmented into two segments. A highly precise AF method based on the combination of the above-described method with phase difference AF is further known.

Japanese Unexamined Patent Application, First Publication No. 2009-261573 discloses a fundus camera that makes precise focusing possible even in cases in which the eye to be examined has an inherent aberration. There are cases in which using only a means that performs AF by using a focus index image will not necessarily result in a focusing state (best focus) on the fundus of the eye, and based on this, phase difference AF is performed after the above-described AF has finished.

In the prior art, in a case in which the contrast of the target of the focusing (blood vessels or the like) is low, there is a possibility that phase difference AF will not be able to be performed in relation to the subject during phase difference AF.

SUMMARY OF THE INVENTION

An apparatus according to one Embodiment of the present invention is an examination apparatus that performs examinations by using an image of the subject captured by an image capturing element, wherein the examination apparatus is provided with a detection unit configured to perform focus detection by detecting the phase differences between a plurality of signals that are acquired from the image capturing element, and a determining unit configured to determine a region in which the focus detection in an angle of view, and in which the apparatus is characterized in that, in a case in which the focus detection precision of a first subject is lower than a threshold, the determining unit determines a search region that passes through the first subject, and determines a region in which a second subject for which the focus detection precision is higher than the threshold is included in the search region as the region in which the focus detection.

Further features of the present invention will become apparent from the following description of exemplary Embodiments with reference to the attached drawings.

BRIEF DESCRIPTION OF THE DRAWINGS

FIGS. 3A and 3B are an approximate plane diagram and an approximate cross section of a pixel of an image capturing element.

FIGS. 8A and 8B are schematic diagrams showing an image of the fundus of the eye made by passing an illumination light through the pupil.

FIGS. 12A to 12C are approximate diagrams showing the enlargement of concentric circle regions in Embodiment 3.

DESCRIPTION OF THE EMBODIMENTS

Exemplary Embodiments of the present invention will be explained in detail below with reference to the attached drawings. In each Embodiment, an example in which the examination apparatus according to the present invention has been applied to an ophthalmic apparatus that performs optical examinations of an eye to be examined will be shown.

Embodiment 1

Figure 1:
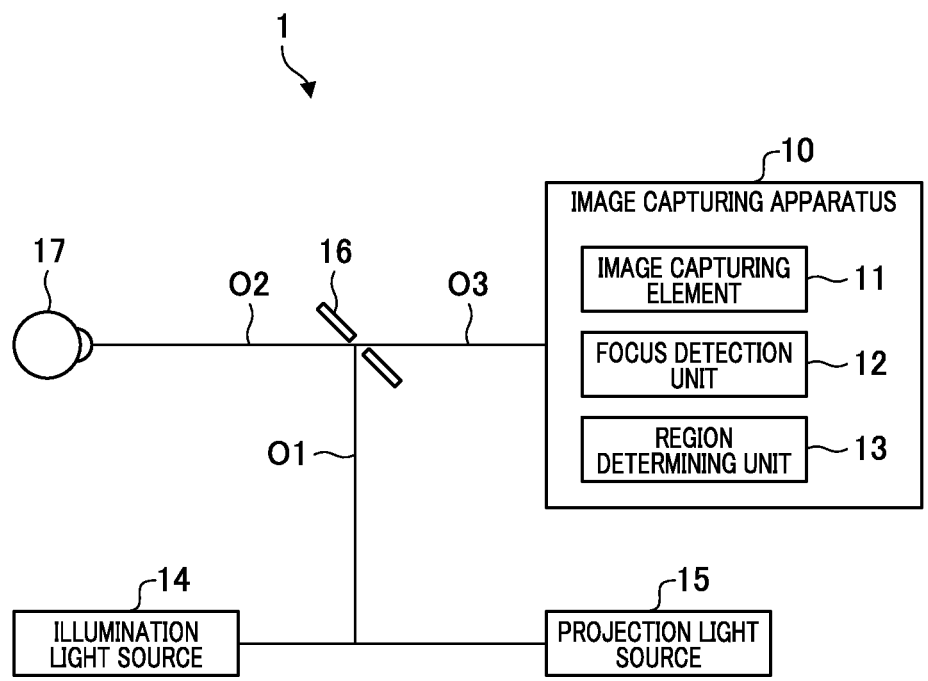
FIG. 1 is an approximate diagram of an ophthalmic apparatus.

FIG. 1 is a diagram that approximately shows the overall structure of an ophthalmic apparatus 1 according to the present Embodiment. An image capturing apparatus 10 is provided with an image capturing element 11, a focus detection unit 12 and a region determining unit 13. First through a third optical axes O1, O2, and O3 in the optical system of the ophthalmic apparatus 1 are shown. An illuminating light source 14 and a projecting light source 15 as well as a perforated mirror 16 are disposed on the first optical axis O1. The illuminating light source 14 is a light source for illuminating an eye to be examined 17. The projecting light source 15 is a light source for projecting a pattern image onto the eye to be examined 17.

Each of the lights that are emitted from the illuminating light source 14 and the projecting light source 15 travel along the first optical axis O1 and reflect off of the perforated mirror 16. The light that is reflected off of the perforated mirror 16 travels along the second optical axis O2, thereby being made incident on the eye to be examined 17. The light that is reflected off of the eye to be examined 17 advances along the second optical axis O2, and passes through the hole of the perforated mirror 16. The light that has passed through the hole of the perforated mirror 16 advances along the third optical axis O3, thereby being made incident on the image capturing unit 10. Note that although not shown in FIG. 1, there is a ring-shaped diaphragm disposed on the optical axis O1, there is an objective lens disposed on the optical axis O2, and optical members such as a focus lens and the like are disposed on the optical axis O3. (Refer to Japanese Unexamined Patent Application, First Publication No. 2009-261573: FIG. 1).

Figure 2:
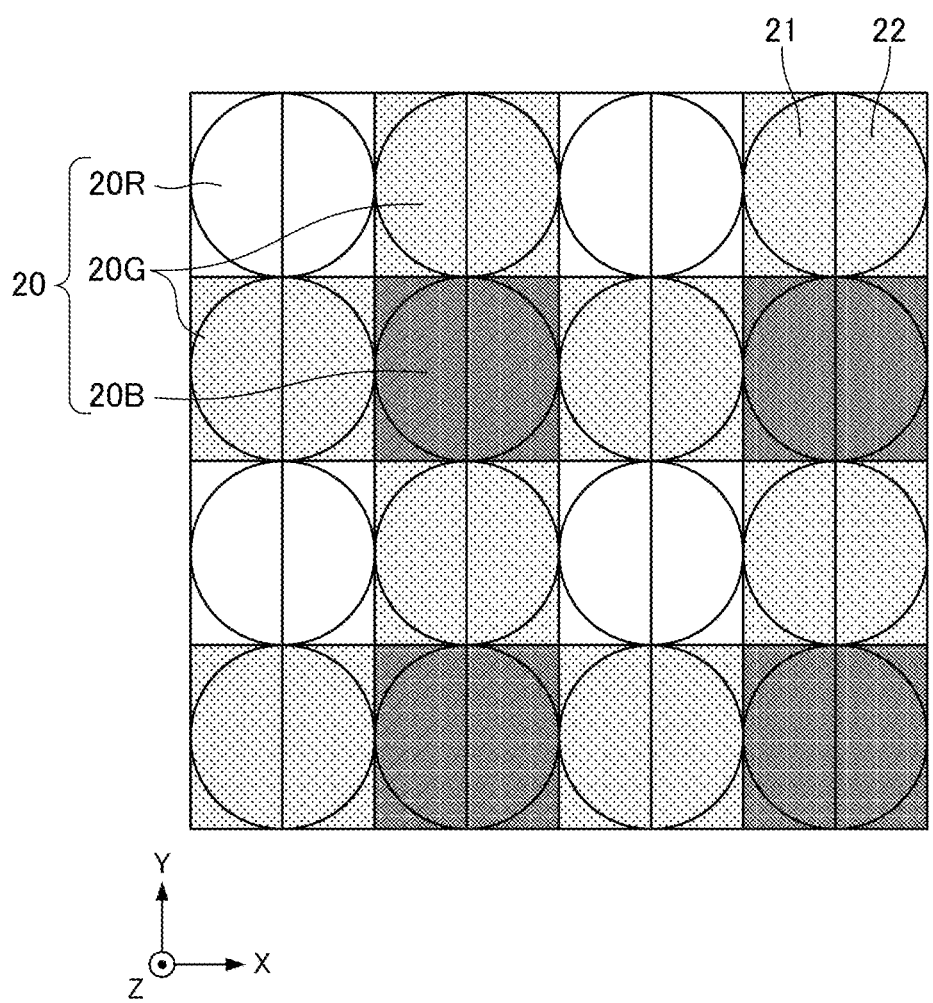
FIG. 2 is an approximate diagram of a pixel array of an image capturing element.

An image capturing pixel array as well as a focus detection pixel array of the image capturing element 11 will now be explained with reference to FIG. 2. FIG. 2 is a diagram of an image capturing pixel array shown in a range of four columns by four rows, and a focus detection pixel array shown in a range of eight columns by four rows, in relation to the pixel arrays of a 2-dimensional CMOS (complementary metal-oxide-semiconductor) image sensor. The direction that is perpendicular to the surface of the paper for FIG. 2 has been defined as the direction of the Z axis, and the direction of the X axis and the direction of the Y axis are each defined as the directions that are orthogonal to the Z axis. The direction of the X axis corresponds to the horizontal direction, and the direction of the Y axis corresponds to the perpendicular direction. The subject side is made the plus side with respect to the direction of the Z axis. In addition, the right side of FIG. 2 is made the plus side with respect to the direction of the X axis, and the upper side of FIG. 2 is made the plus side with respect to the direction of the Y axis.

A pixel group 20, which is 2 columns by 2 rows and is shown in FIG. 2, is configured by pixels 20R, 20G, and 20B, which have differing spectral sensitivity.

The pixel 20R has R (Red) spectral sensitivity, and is positioned in the upper left of the pixel group 20.

The pixels 20G have G (Green) spectral sensitivity, and are positioned in the upper right and lower left of the pixel group 20.

The pixel 20B has B (Blue) spectral sensitivity, and is positioned in the lower right of the pixel group 20.

Furthermore, each pixel is configured by a first focus detection pixel 21 and a second focus detection pixel 22 that have been arranged in a two column by one row array. That is, the inside of one pixel is a configuration that has a plurality of focus detection pixels. Acquisition of not just the image capturing image signal but also the focus state detection signal is made possible by a configuration in which the four column by four row image capturing pixels (the eight column by four row focus detection pixels) that are shown in FIG. 2 are disposed in large numbers on a plane.

FIGS. 3A and 3B are diagrams that schematically show the structure of the pixel unit that configures the image capturing element. FIG. 3A is a plane figure of one pixel 20G of the image capturing element that is shown in FIG. 2 as viewed from the light receiving side (+Z side) of the image capturing element. FIG. 3B is a cross section diagram of the cross section at the a-a line in FIG. 3A as viewed from the −Y side.

As shown in FIGS. 3A and 3B, a microlens 35 for collecting incident light is formed on the light receiving side of each pixel unit. In the pixel unit of the pupil segmentation configuration, the segmentation number in the direction of the X axis is expressed as NH, and the segmentation number in the direction of the Y axis is expressed as NV. FIGS. 3A and 3B show examples in which NH=2 and NV=1, and a photoelectric converter 31 and a photoelectric converter 32 are formed. The photoelectric convertor 31 and the photoelectric convertor 32 each correspond to the first focus detection pixel 21 and the second focus detection pixel 22.

For example, the photoelectric converters 31 and 32 have a pin structure photodiode in which an intrinsic layer is interposed between a p-type layer and an n-type layer. In addition, the intrinsic layer may be omitted, and may be formed as a p-n junction photodiode according to necessity. In each pixel unit, a color filter 36 is formed between the microlens 35 and the photoelectric convertors 31 and 32. Alternatively, the spectral transmittance of the color filters may be changed for each photoelectric convertor, or the color filters may be omitted, according to necessity.

The light that is incident on the pixels 20 G in FIGS. 3A and 3B is collected by the microlens 35, and after being spectrally dispersed by the color filters 36, is received by each of the photoelectric converters 31 and 32. In the photoelectric convertors 31 and 32, electrons and holes are produced in pairs according to the amount of light received, and the minus charge electrons are accumulated in the n-type layer (not shown) after separation in the depletion layer. In contrast, the holes (positive holes) are ejected to the outside of the image capturing element 11 via the p-type layer, which is connected to a constant voltage source (not shown). The electrons that have been accumulated in the n-type layers (not shown) of the photoelectric converter 31 and the photoelectric converter 32 are transferred to an electrostatic capacitance unit (FD) via a transfer gate, and are converted into a voltage signal.

Figure 4:
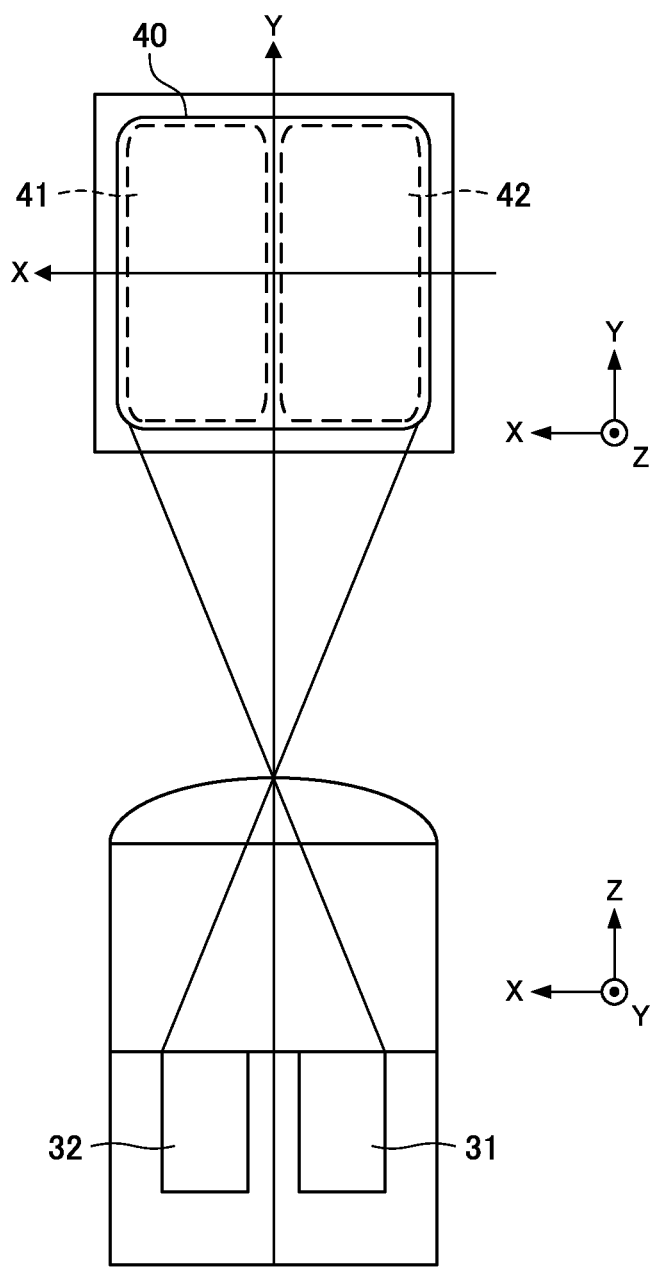
FIG. 4 is an approximate explanatory diagram showing the relationship between a pixel in an image capturing element and a pupil segmentation.

FIG. 4 is an approximate explanatory diagram that shows the corresponding relationship between the pixel structure and a pupil segmentation in FIGS. 3A and 3B. FIG. 4 shows a cross sectional diagram of the cross section at the a-a line of the pixel structure that is shown in FIG. 3A as viewed from the +Y side, and the pupil surface (pupil distance DS) of the image capturing element 11. In FIG. 4, in order to correspond to the coordinate axis of the pupil surface of the image capturing element 11, the direction of the X axis and the direction of the Y axis in the cross-sectional diagram are the reverse of those in FIGS. 3A and 3B. The image capturing element 11 is disposed in the vicinity of the image formation surface of the image capturing optical system, and the light from the subject passes through a pupil region 40 of the image capturing optical system, and is made incident on each pixel. The pupil region 40 is a pupil region which can receive light on all the pixels 20G when all of the photoelectric converters 31 and the photoelectric converters 32 (corresponding to the first and second focus detection pixels 21, and 22) are combined.

The center of gravity of a first pupil portion region 41, which corresponds to the first focus detection pixel 21 in FIG. 4, is made eccentric towards the +X side on the pupil surface. The first pupil portion region 41 is made approximately conjugate with the light receiving surface of the photoelectric converter 31, for which the center of gravity is made eccentric towards the −X side, by a microlens. That is, the first pupil portion region 41 represents the pupil region in which the first focus detection pixel 21 can receive light. In addition, the center of gravity of a second pupil portion region 42, which corresponds to the second focus detection pixel 22, is made eccentric towards the—X side on the pupil surface. The second pupil portion region 42 is made approximately conjugate with the light receiving surface of the photoelectric converter 32, for which the center of gravity is made eccentric towards the +X side, by a microlens. That is, the second pupil portion region 42 represents the pupil region in which the second focus detection pixel 22 can receive light.

In image capturing surface phase difference AF, pupil segmentation is performed by using a microlens of an image capturing element, and therefore, is influenced by diffraction. For example, in contrast to the pupil distance DS to the pupil surface of the image capturing element in FIG. 4 being several tens mms (millimeters), the diameter of the microlens is several μms (micrometers). The aperture value of the microlens thereby becomes tens of thousands, and a diffraction blur of a level of several tens of mms occurs. Thus, the image from the light receiving surface of the photoelectric converters acquires light reception sensitivity (the incident angle distribution of the light receiving rate), without being a clear pupil region or pupil portion region.

Figure 5:
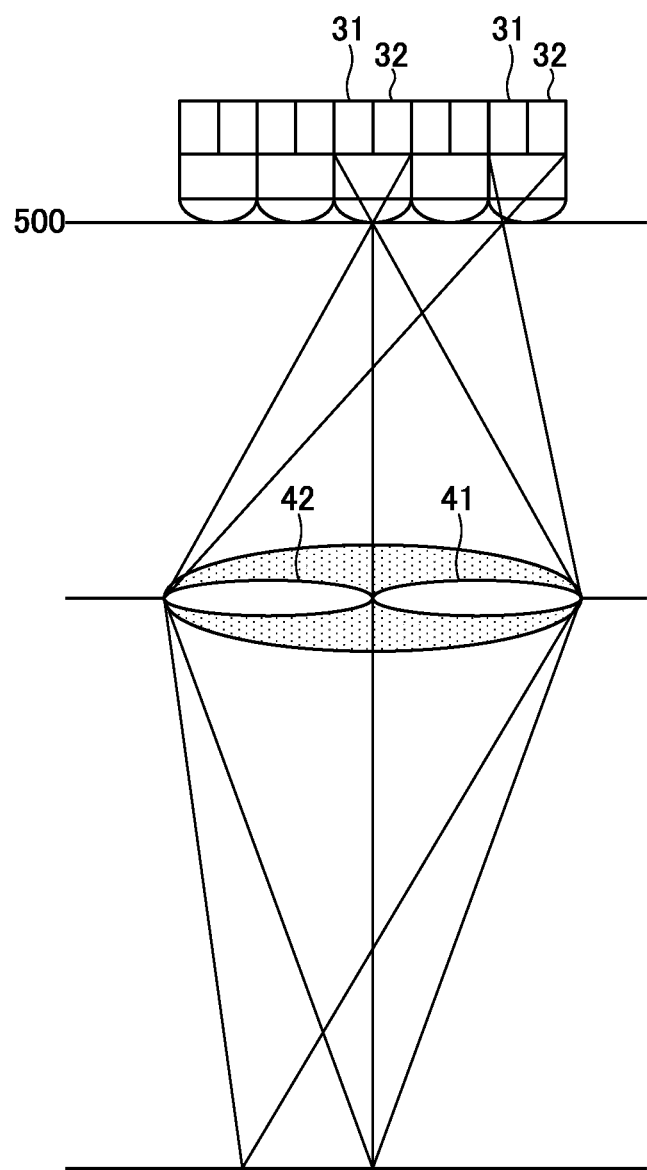
FIG. 5 is an approximate explanatory diagram showing an image capturing element and a pupil portion region.

FIG. 5 is an approximate diagram that shows the corresponding relationship between the image capturing element and the pupil portion region of the present Embodiment. The light that passes through each of the first and second pupil portion regions 41 and 42 becomes incident on each pixel unit of the image capturing element at different angles, and the first and second photoelectric converters 31 and 32 receive light from an incident surface 500. In the present Embodiment, an example is shown in which the pupil region has been pupil segmented into two segments in the horizontal direction. There are Embodiments in which, according to necessity, pupil segmentation into four or nine segments is performed in the perpendicular direction.

The image capturing element 11 is a structure in which a plurality of pixel units having first and second focus detection pixels are arranged. For example, the first photoelectric converter 31 outputs an A image signal by receiving the light that passes through the first pupil portion region 41 of the image capturing optical system. The second photoelectric converter 32 outputs a B image signal by receiving the light that passes through the second pupil portion region 42 of the image capturing optical system. The defocus amount can be obtained by detecting the phase difference between the A image signal and the B image signal. In addition, the image capturing pixels output an A+B image signal by receiving the light that passes through the pupil region 40, which is a combination of the first and second pupil portion regions of the image capturing optical system.

In the present Embodiment, an example has been explained in which the image capturing pixels are configured from a first and a second focus detection pixel. The first and the second focus detection pixels may also be made pixel configurations that are separate from the image capturing pixels according to necessity. In this case, the configuration is one in which the first focus detection pixel and the second focus detection pixel are partially disposed on a portion of the pixel array.

In addition, in the present Embodiment, the first focus detection signal (the A image signal) is generated from the light receiving signal of the first focus detection pixel of each pixel, and the second focus detection signal (the B image signal) is generated from the light receiving signal of the second focus detection pixel of each pixel, and focus detection is performed. A signal is generated in which the resolution corresponds to the image capturing image of the number N of effective pixels for each of the pixels of the image capturing element by adding the light receiving signal of the first focus detection pixel 21 and the light receiving signal of the second focus detection pixel 22. For example, as the signal generation method, there is also a method that generates the second focus detecting signal from the difference of the image capturing signal and the first focus detection signal. In this case, for example, the A image signal and the A+B image signal are obtained, and the B image signal is generated by subtracting the A image signal from the A+B image signal.

Figure 6:
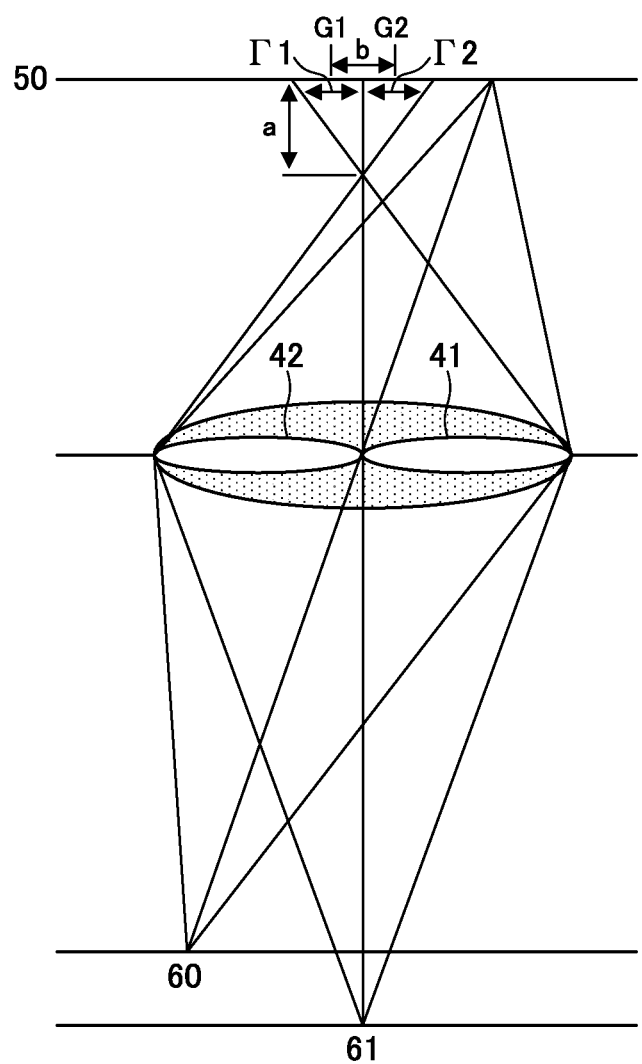
FIG. 6 is an approximate relational diagram of a defocus amount and an image shift amount.

The relationship between the defocus amount and the image shift amount according to the first and second focus detection signals that have been obtained by the image capturing element will now be explained with reference to FIG. 6. FIG. 6 is a relational diagram that approximately shows the defocus amount (expressed as a) and the image shift amount between the focus detection signals. The image capturing element (not shown) is disposed on an image capturing surface 50, and, in the same manner as in FIG. 4 and FIG. 5, the pupil surface of the image capturing optical system is segmented into two segments, the first pupil portion region 41 and the second pupil portion region 42.

The size a of the defocus amount a represents the distance from the image forming position of the subject image to the image capturing surface 50. The reference numeral for the defocus amount a is made a negative reference numeral (a<0) in the front focus state, in which the image forming position of the subject image is more towards the subject side than the image capturing surface 50, and a positive reference numeral (a>0) in the back focus state, in which the image forming position of the subject image is more towards the side that is opposite to the subject than the image capturing surface 50. In the focus state in which the image forming position of the subject image is on the image forming surface (focus position), a=0. The subject 60 in FIG. 6 shows an example of the focus state (a=0), and the subject 61 shows an example of the front focus state (a<0). The defocus state (|a|>0) is made by combining the front focus state (a<0) and the back focus state (a>0).

In the front focus state (a<0), from among the light flux from the subject 61, the light flux that have passed through the first pupil portion region 41 (or the second pupil portion region 42) spread out to a width Γ1 (or Γ2) with the center of gravity position G1 (or G2) of the light flux as the center once it has been collected. In this case, the image on the image capturing surface 50 becomes a blurred image. The blurred image receives light from the first focus detection pixel 21 (or the second focus detection pixel 22) that configures each of the pixels that have been arranged in an array in the image capturing element, and a first focus detection signal (or a second focus detection signal) is generated. Thus, the first focus detection signal (or the second focus detection signal) is stored in a memory as the image data for a subject image (a blurred image) having the width Γ1 (or Γ2) at the center of gravity position G1 (or G2) on the image capturing surface 50. As the size |a| of the defocus amount a increases, the width Γ1 (or Γ2) increases in an approximately proportionate manner. In the same manner, a size |b| of an image shift amount b (=the difference of the center of gravity positions "G1-G2" of the light flux) of the subject image between the first focus detection signal and the second focus detection signal also increases in an approximately proportionate manner as the size |a| of the defocus amount increases. Note that although in the back focus state (a>0), the direction of the image shift of the subject image between the first focus detection signal and the second focus detection signal is the opposite of that in the front focus state, they both have the same tendency.

The size of the image shift amount between the first focus detection signal and the second focus detection signal increases as the size of the defocus amount of the first image focus detection signal and the second image focus detection signal, or of the image capturing signal, which is the sum of the first focus detection signal and the second focus detection signal, increases. Therefore, the focus detection unit 12 calculates the defocus amount based on a relationship in which the size of the image shift amount between the first focus detection signal and the second focus detection signal increases as the size of the defocus amount of the image capturing signal increases. That is, the image shift amount can be converted to the detected defocus amount by using a conversion coefficient that has been calculated based on the baseline length that represents the separation between the centers of gravity of the first pupil portion region 41 and the second pupil portion region 42.

Next, focus detection precision for a case in which phase difference AF is performed in an ophthalmic apparatus that captures images of the fundus of the eye will be described. In this case, there is a tendency for the focus detection precision to become low in comparison to a case in which phase difference AF is performed in a general use digital camera. There are cases in which the reflection rate of the fundus of the eye is several percent lower, and when the subject is compared to that of a case in which phase difference AF is performed in a general use digital camera and the like, there is a tendency for the contrast of the subject to be difficult to maintain. When the contrast of the subject is low, it is possible that when the image shift amount that was explained in FIG. 6 is calculated, the signal will be obscured by noise. For example, it is possible that the focus detection precision will decrease due to reasons such as a false focus occurring. In addition, in the ophthalmic apparatus 1 that was explained in FIG. 1, a circular vignetting is created on the light flux from inside of the ophthalmic device by the perforated mirror 16. Due to this, the light flux that reaches the focus detection unit 12 becomes narrow, that is, the F value becomes large. The focus detection precision decreases due to the image shift amount that was explained in FIG. 6 becoming smaller.

Figure 7:
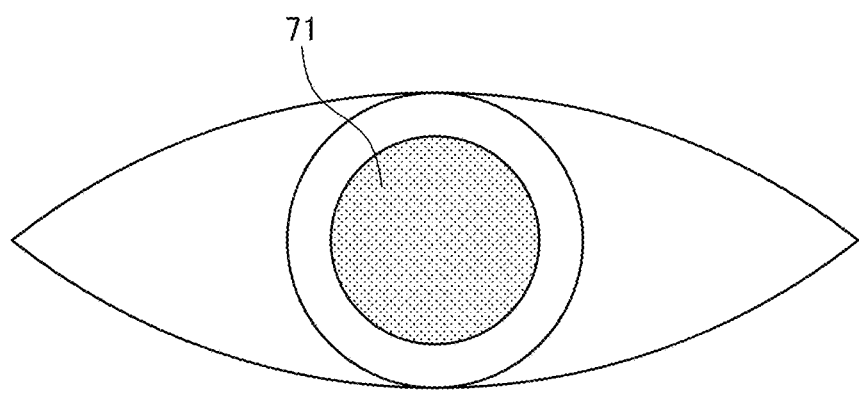
FIG. 7 is an approximate diagram of the pupil of an eye to be examined.

FIG. 7 is a schematic diagram showing the eye to be examined including a pupil 71. From among the light from the illumination light source 14 and the projection light source 15, only the light that has passed through the pupil 71 reaches the fundus of the eye. FIGS. 8A and 8B are schematic diagrams showing an image of the fundus of the eye made by the light from the illumination light source 14 that has passed through the pupil 71. However, in the present Embodiment, it is assumed that the optical axis of the eyeball matches the optical axis of the ophthalmic apparatus 1. An angle of view 81 shows a circular shape due to vignetting of light flux caused by the perforated mirror 16.

Various blood vessels exist in the fundus of the eye. However, in FIGS. 8A, and 8B, blood vessels of the fundus of the eye are shown as a subject 82 and a subject 85. The subject 82 is one blood vessel that exists in the fundus of the eye that the user (the examiner) has selected to be the subject of the focusing, and is included in a region 83. In order to focus on the subject 82, the focus detection unit 12 performs the focus detection that was explained in FIG. 5 inside the region 83.

In this context, the processing method for a case in which the focus detection precision does not fulfill an established precision (a threshold precision) will now be explained. For example, a case will be assumed in which the focus detection precision for the subject 82 does not fulfill the established precision. In this case, the region determining unit 13 will determine a circle 84 (refer to the dotted line) that passes through the region 83. In a case in which the optical axis of the eyeball and the optical axis of the ophthalmic apparatus 1 match, the portion with the same center as the angle of view, which is circular due to vignetting caused by the perforated mirror 16 will be the circle 84. The eyeball can be approximated as a spherical shape, and therefore, as shown in in FIGS. 8A, and 8B, in a case in which the optical axis of the eyeball and the optical axis of the ophthalmic apparatus 1 match, the defocus amount on the circle 84 that passes through the region 83 will be the same defocus amount as that of the region 83. Even if the user intends to focus on the subject 82 that is included in the region 83, it is possible that a sufficient focus detection precision cannot be obtained, due to reasons such as the contrast of the subject 82 being low and the like. In this case, the focus detection unit 12 will perform focus detection in a region 86, which is on the circle 84. The region 86 is on the circle 84, and satisfies the established focus detection precision, as well as being a region that includes a subject 85 for which the focus detection precision is higher than that for the subject 82. Focusing is implemented on the subject 85 by the drive control of the focus lens.

In FIG. 8A, it was explained that the defocus amount for the circle 84 and the defocus amount for the region 83 are the same. However, this is not limiting, and the region 83 may also be treated as a region with the same defocus amount as a concentric circle region 87 that is shown in FIG. 8B based on the required precision desired by the user. That is, the concentric circle region 87, which is made the border between the two concentric circles, is a region with a width d with the same center as the circle 84 that passes through the region 83. The inside of the concentric circle region 87 can be treated as being within the required precision and to have the same defocus amount. Thus, in a case in which the user would like to focus on the subject 82, which is included in the region 83, they may focus on the subject 85 in the concentric circle region 87. It is thereby possible to obtain the same defocus amount for the subject 82 within the required precision.

Figure 9:
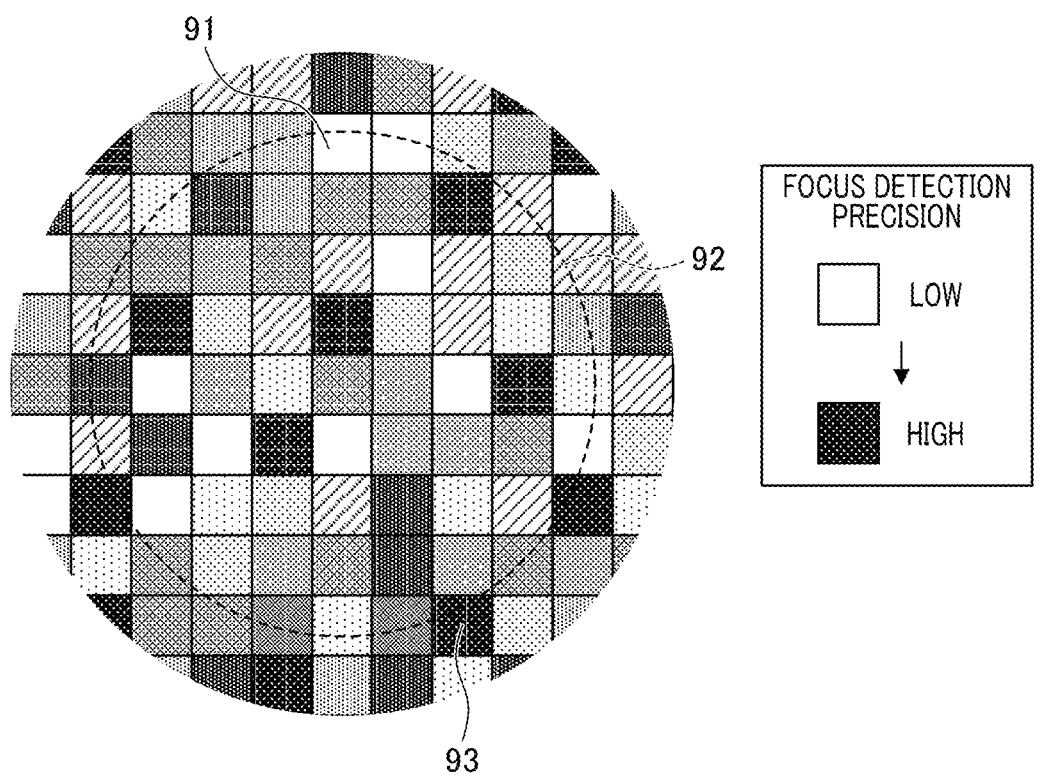
FIG. 9 is a schematic diagram showing an example of a focus detection precision map.

The determination method for the subject 85 and the region 86 of FIGS. 8A and 8B will now be explained with reference to FIG. 9. FIG. 9 is a diagram that schematically shows an example of a focus detection precision map based on a defocus map that has been calculated by the focus detection unit 12. The level of the focus detection precision is shown by a grayscale. A region 91 and a region 93 are regions that respectively correspond to the region 83 and the region 86 of FIGS. 8A and B. A circle 92 corresponds to the circle 84 in FIGS. 8A and 8B. Note that although they have been omitted, the region 91 and the region 93 each include different subjects (blood vessels).

It is assumed that the subject that is included in the region 91 of FIG. 9 does not fulfill the established precision for reasons such as, for example, the contrast being low or the like. That is, it is assumed that the user has selected the region 91, which includes a subject for which the focus detection precision is low. In a case such as this, processing is performed on the focus detection precision map to determine the region 93, which is on the circle 92 that passes through the region 91, and in which the subject that has the highest focus detection precision is included. Alternatively, a region that has a fixed width such as the concentric circle region 87 that is shown in FIG. 8B may be used instead of the circle 92. In this case, processing is performed to determine the region within the concentric circle region in which the subject with the highest focus detection precision is included.

Figure 10:
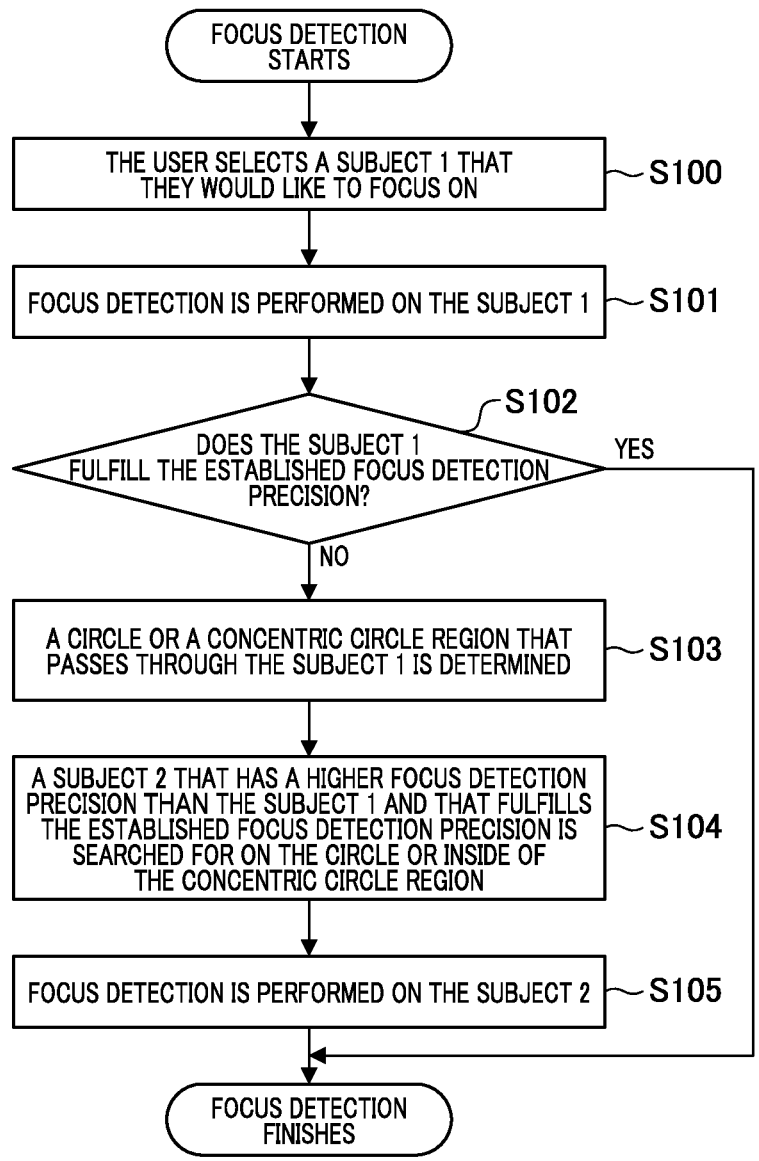
FIG. 10 is a flowchart showing the processing for a case in which phase difference AF is performed

The processing in the present Embodiment will now be explained with reference to FIG. 10. FIG. 10 is a flowchart for a case in which phase difference AF is performed. The following processing is, for example, realized by the execution of a program by the CPU (central processing unit) in the ophthalmic apparatus or in the image capturing apparatus. When the focus detection processing starts, in S100, selection processing for the subject is carried out by a user operation. In this context, it is assumed that a subject 1 has been selected. Next, in S101, the focus detection unit 12 performs focus detection on the subject 1. Then, in S102, the focus detection unit 12 will identify whether or not the focus detection precision for the subject 1 is higher than the threshold. In a case in which it has been identified that the focus detection precision for the subject 1 is higher than the threshold, and fulfills the established focus detection precision, the process will proceed to S106, and the focus detection processing will end. In a case in which it has been identified that the predetermined precision has not been fulfilled, the process will proceed to S103.

In S103, the region determining unit 13 will determine the circle (refer to FIG. 8A: 84) or concentric circle region (refer to FIG. 8B: 87) that passes through the region in which the subject 1 is included. Next, in S104, the region determining unit 13 searches for a subject 2 that has a higher focus detection precision than the subject 1 which is on the circle or is inside the concentric circle region that was determined in S103 and which fulfills the established focus detection precision. In S105, in a case in which a subject 2 has been determined by the search, the focus detection unit 12 will perform focus detection for the subject 2. The AF frame (focus detection frame) that corresponds to the region that includes the subject 2 is then displayed. Subsequently, the process proceeds to S106, and the focus detection finishes. After the focus detection is performed, the control unit provided with the ophthalmic apparatus 1 or the image capturing apparatus 10 will control the drive mechanism unit of the focus lens, and focus adjustment (phase difference AF) will be performed by moving the focus lens on the optical axis O3. AF control is well-known, and the explanation thereof has therefore been omitted.

The provision of an ophthalmic apparatus that can perform phase difference AF on an arbitrary subject in an eye to be examined and focus thereon is made possible by the present Embodiment.

Embodiment 2

Next, Embodiment 2 of the present invention will be explained. In Embodiment 1, a case in which the optical axis of the eye to be examined and the optical axis of the ophthalmic apparatus match was explained. However, the present Embodiment shows a resolution method for when these optical axes do not match. Only the points of difference between the present Embodiment and Embodiment 1 will be explained, and redundant explanations will be omitted. A similar method of omission will be used for all of the following Embodiments.

Figure 11C:
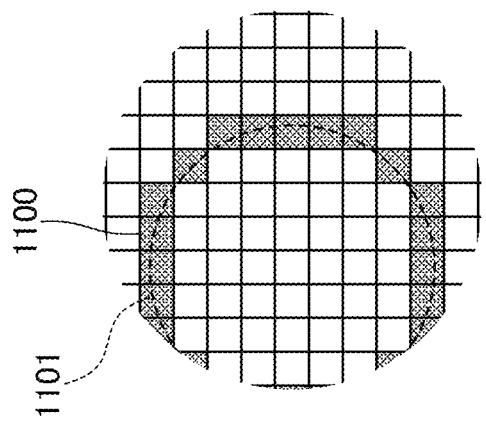
FIGS. 11A to 11C are schematic diagrams showing examples of focus detection precision maps in Embodiment 2.
Figure 11B:
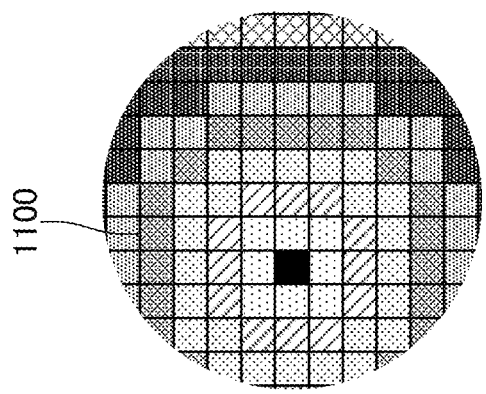
Figure 11A:
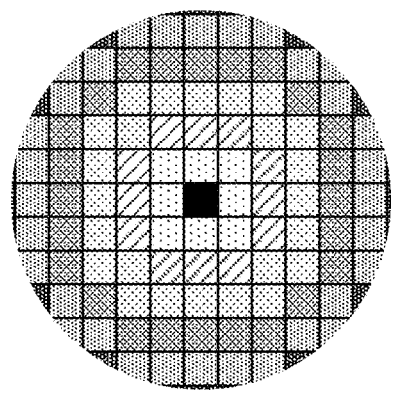

FIG. 11A shows an example of a focus detection precision map based on a defocus map for a case in which the optical axis of the eye to be examined and the optical axis of the ophthalmic apparatus match. FIG. 11B shows an example of a focus detection precision map based on a defocus map for a case in which the optical axis of the eye to be examined and the optical axis of the ophthalmic device do not match. In the case of FIG. 11B, the region that has the same defocus amount is a circle region that is centered on a position differing from the angle of view, and is an arc-shaped region within the angle of view. An area 1100 shows the region in which the subject that has been selected by the user is included.

In FIG. 11C, only a portion of the region (arc) that has been deemed to have the same defocus amount as the defocus amount of the region 1100 is shown by separating it. A circle 1101 is a circle in a case in which, for example, the method of least squares or the like has been used to form an approximate circle, and corresponds to the circle 84 in FIGS. 8A and 8B. In addition, in the same manner as in the case of Embodiment 1, a concentric circle region may be used instead of a circle according to the required precision. In S104 in FIG. 10, the region determining unit 13 searches on the circle 1101 for a subject that has a higher focus detection precision than the subject that has been selected by the user, and which also fulfills the established focus detection precision.

Focusing on an arbitrary subject in an eye to be examined is made possible by the present Embodiment even in a case in which the optical axis of the eye to be examined and the optical axis of the ophthalmic device do not match.

Embodiment 3

An Embodiment 3 of the present invention will now be explained with reference to FIGS. 12A to 12C. In the above disclosed Embodiments, focus detection is performed on a separate subject 2 from on a circle or inside a concentric circle region in a case in which the focus detection precision for the subject 1 that has been selected by the user does not fulfill the established focus detection precision. However, a case in which the subject 2 also does not satisfy the established focus detection precision is possible. Accordingly, the present Embodiment shows an example of processing for enlarging the circle or the concentric circle region.

FIGS. 12A to 12C are schematic diagrams that show the enlarged state of a concentric circle region. FIG. 12A and FIG. 12B each correspond to FIG. 8A and FIG. 8B, and therefore detailed descriptions thereof have been omitted. FIG. 12C shows a state in which the width of the concentric circle region 87 of FIG. 12B has been increased to extend up to the concentric circle region 1203. Note that it is also possible to further widen the concentric circle region 1203 to the entire region of the angle of view.

In S104 in FIG. 10, the region determining unit 13 performs a search inside the enlarged concentric circle region for a subject 1201, which has a higher focus detection precision than that of the subject 82, and which fulfills the predetermined focus detection precision. As a result of this, focus detection is performed on the region 1202 in which the subject 1201 is included. Note that it is also possible for the processing of S104 in FIG. 10 to be executed while the ophthalmic apparatus automatically widens the concentric circle region that has been explained in the present Embodiment. In addition, in a case in which processing for automatically lowering the established focus detection precision is executed accompanying the enlargement of the concentric circle region, processing to notify the user of the change in the focus detection precision will be performed.

Focusing on an arbitrary subject in an eye to be examined by enlargement processing of a circle or a concentric circle region is made possible by the present Embodiment.

Embodiment 4

Figure 13:
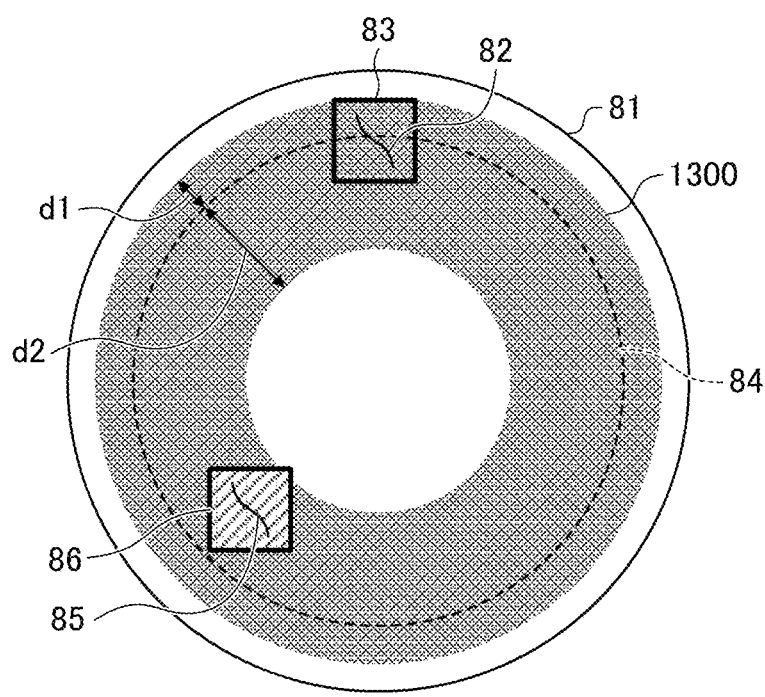
FIG. 13 is an approximate diagram showing the enlarged width of a concentric circle region in Embodiment 4.

An Embodiment 4 of the present invention will now be explained with reference to FIG. 13. In the present Embodiment, a method for making the enlarged width in the periphery direction and the central direction of the angle of view differ in relation to the enlargement processing for the concentric circle region is shown. FIG. 13 shows an example of a concentric circle region 1300 in which enlargement to a width d1 in the periphery direction of the angle of view and to a width d2 on the central side has been performed on the circle 84.

In image capturing surface phase difference AF, the focus detection precision generally becomes lower towards the peripheral regions, and therefore, a concentric circle region is enlarged as "d1<d2" so that the subject search (FIG. 10: S104) is preferentially performed in a range near the center of the angle of view.

Focusing on an arbitrary subject in an eye to be examined by enlargement processing for different widths in the periphery direction and the central direction of the angle of view is made possible by the present Embodiment.

Embodiment 5

An Embodiment 5 of the present invention will now be explained with reference to FIG. 14. The present Embodiment shows a countermeasure for a case in which a subject that fulfills the established focus detection precision does not exist even when the concentric circle region is enlarged to the entire surface of the angle of view 81. In this case, the present Embodiment performs pattern projection on the eye to be examined.

Figure 14:
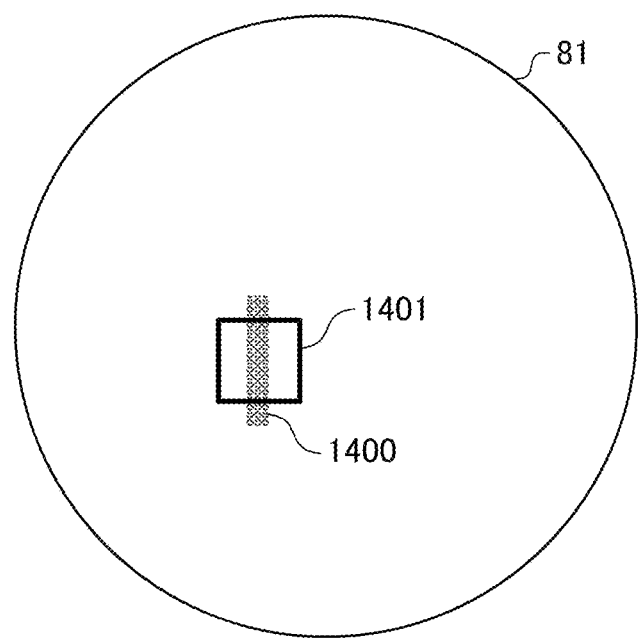
FIG. 14 is an approximate diagram of focus detection using pattern projection in Embodiment 5.

FIG. 14 shows the state of the pattern projection being performed on the eye to be examined by the projection light source 15. For example, the eye to be examined is irradiated by an infrared light band pattern light. Focus detection is performed on the region 1401 that includes the vertically striped projection image 1400 in the angle of view 81.

Focusing on an arbitrary subject in an eye to be examined by performing the projection of a fixed pattern is made possible by the present Embodiment.

Preferred Embodiments of the present invention have been explained above, however, the present invention is not limited by these Embodiments, and various modifications or alterations can be made within the scope of the essentials thereof.

Other Embodiments

In the above-described Embodiments, an example is shown in which, in an optical examination apparatus for an eye to be examined, a circle and a concentric circle region are used as a search region that passes through a first subject in a case in which the focus detection precision of the first subject is lower than a threshold. However, without being limited thereby, the region determining unit 13 will determine a compatible shape (for example, an ellipsis or a polygon) as the search region of the subject according to the examination subject. In a case in which a second subject for which the focus detection precision is higher than the threshold is detected in the search region that has been determined, focus detection will be performed on the region in which the second subject is included.

In addition, there is an Embodiment in which 3 or more projections are performed by the light source. In this case, the ophthalmic apparatus 1 is able to control the rotation or the extinguishing of the working dots. Alternatively, there is an Embodiment in which circular pattern projection is performed by the light source.

While the present invention has been described with reference to exemplary Embodiments, it is to be understood that the invention is not limited to the disclosed exemplary Embodiments. The scope of the following claims is to be accorded the broadest interpretation so as to encompass all such modifications and equivalent structures and functions.

This application claims the benefit of Japanese Patent Application No. 2021-014432, filed Feb. 1, 2021 which is hereby incorporated by reference herein in its entirety.

What is claimed is:

1. An examination apparatus that performs examinations using an image of a subject captured by an image capturing element, the examination apparatus comprising:
   a detection unit configured to perform focus detection by detecting the phase difference between a plurality of signals that are acquired from the image capturing element, and
   a determining unit configured to determine a region in which to perform the focus detection in an angle of view,
   wherein in a case in which the focus detection precision of a first subject is lower than a threshold, the determining unit determines a search region that passes through the first subject, and determines a region in which a second subject for which the focus detection precision is higher than the threshold is included in the search region as the region in which the focus detection.

2. The examination apparatus according to claim 1, wherein
   the detection unit calculates a defocus amount by detecting the phase difference of the plurality of signals, and
   the determining unit determines a circle or a concentric circle region as the search region from the focus detection precision based on the defocus amount.

3. The examination apparatus according to claim 1, wherein
   in a case in which the focus detection precision for the first subject is lower than a threshold, the detection unit performs focus detection on the second subject that is included in the region that has been determined by the determining unit.

4. The examination apparatus according to claim 2, wherein
   the determining unit changes the size of the concentric circle region.

5. The examination apparatus according to claim 4, wherein
   the determining unit changes the size of the concentric circle region to different widths in the central direction and the periphery direction of the angle of view.

6. The examination apparatus according to claim 1 further comprising a projection unit configured to project a pattern light in a case in which the focus detection precision is lower than a threshold.

7. The examination apparatus according to claim 1, wherein the image capturing element further comprises a plurality of microlenses, and a plurality of photoelectric converters corresponding to each microlens.

8. An ophthalmic apparatus characterized in that it performs examinations of an eye to be examined by using the examination apparatus according to claim 1.

9. A control method that is executed in an examination apparatus that performs examinations by using an image of a subject that has been captured by an image capturing element, the control method comprising:
   performing focus detection by detecting the phase difference between a plurality of signals that are acquired from the image capturing element,
   determining a region in which to perform the focus detection in an angle of view, and
   in a case in which the focus detection precision of a first subject in the detection is lower than a threshold, in the determination, a search region that passes through the first subject is determined and processing is performed to determine a region that includes a second subject for which the focus detection precision is higher than the threshold in the search region as the region in which the focus detection.

* * * * *